United States Patent
Koyama et al.

(10) Patent No.: US 6,310,343 B1
(45) Date of Patent: Oct. 30, 2001

(54) ELECTRON IMPACT ELASTIC RECOIL HYDROGEN ATOM ANALYZER

(75) Inventors: Akio Koyama; Tsuyoshi Horiki, both of Wako; Akira Yoneda, Nerima-Ku, all of (JP)

(73) Assignee: Riken, Wako (JP)

( * ) Notice: Subject to any disclaimer, the term of this patent is extended or adjusted under 35 U.S.C. 154(b) by 0 days.

(21) Appl. No.: 09/492,745

(22) Filed: Jan. 27, 2000

(30) Foreign Application Priority Data

Jan. 27, 1999 (JP) .................................................. 11-018651

(51) Int. Cl.[7] .............................. G01N 23/00; G21K 7/00
(52) U.S. Cl. .......................... 250/310; 250/310; 250/294; 250/299; 250/427; 250/492.3
(58) Field of Search .................................. 250/310, 294, 250/299, 427, 492.3

(56) References Cited

U.S. PATENT DOCUMENTS 4,352,985 * 10/1982 Martin ................................... 250/306
4,393,311 * 7/1983 Feldman et al. .................. 250/459.1
5,528,034 * 6/1996 Yamazaki et al. .................... 250/309

* cited by examiner

*Primary Examiner*—Teresa M. Arroyo
*Assistant Examiner*—Anthony Quash
(74) *Attorney, Agent, or Firm*—Jacobson Holman, PLLC

(57) ABSTRACT

An electron impact elastic recoil hydrogen atom analyzer includes an electron gun that projects an electron beam on a surface of a specimen for electron bombardment to make hydrogen atoms contained in the specimen elastically recoil, a hydrogen detecting unit that detects hydrogen atoms emitted from the specimen, and a data processing unit that determines a depth-distribution of hydrogen in the specimen on the basis of data provided by the hydrogen detecting unit. The hydrogen detecting unit includes an ionizer for ionizing hydrogen atoms emitted from the specimen, a deflector for energy analysis of hydrogen ions, and an electron multiplying channel plate for detecting the deflected hydrogen ions.

11 Claims, 2 Drawing Sheets

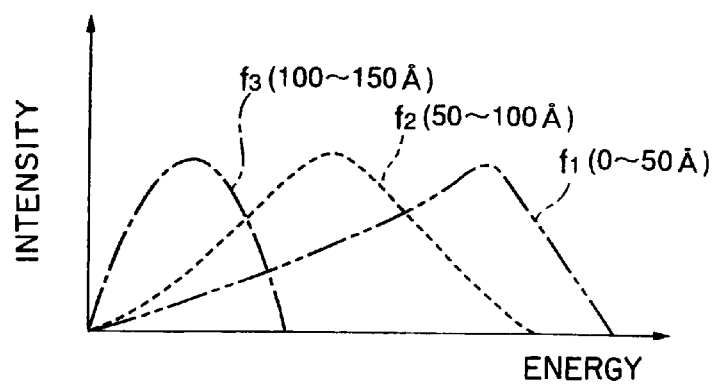
F I G. 2
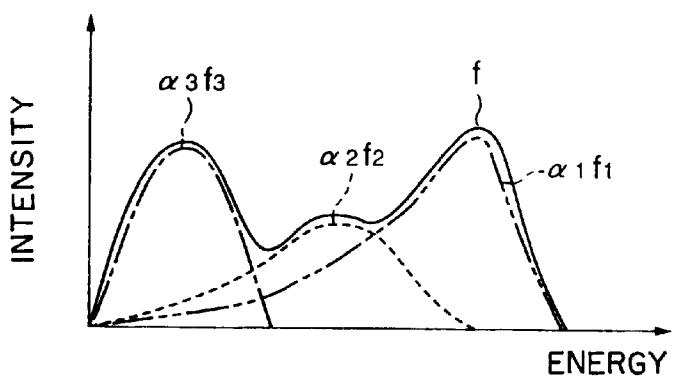
F I G. 3A
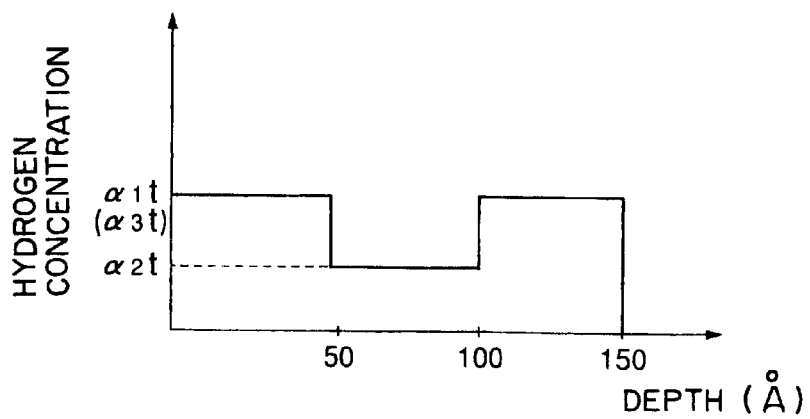
F I G. 3B

ELECTRON IMPACT ELASTIC RECOIL HYDROGEN ATOM ANALYZER

BACKGROUND OF THE INVENTION

1. Field of the Invention

The present invention relates to a hydrogen atom analyzer for analyzing hydrogen distribution in a specimen containing hydrogen. More particularly, the present invention relates to an electron impact elastic recoil hydrogen atom analyzer for analyzing hydrogen distribution in a specimen containing hydrogen by measuring elastic recoil hydrogen atoms emitted from the specimen by electron impact.

2. Description of the Related Art

Hydrogenated semiconductors containing hydrogen are used prevalently as materials for solar cells, liquid crystal displays, video cameras, telecopying sensors and the like. Quality improvement of such hydrogenated semiconductors has become important in recent years. Accurate analysis of hydrogen distribution at the surface and interior places of a sample hydrogenated semiconductor, and the accurate control of hydrogen distribution in the hydrogenated semiconductor are very important for the improvement of the quality of the hydrogenated semiconductor. Practically, it is desirable that the analysis of hydrogen distribution in the sample can simply be achieved and that manufacturing conditions for manufacturing the hydrogenated semiconductor can precisely be controlled through the in situ observation of the manufacturing process.

Incidentally, an Auger electron spectrometric method is a generally known surface analyzing method for analyzing the surface of a specimen, capable of simply achieving the qualitative and quantitative analysis of elements in the surface of a specimen through in situ observation. Although the Auger electron spectrometric method is applied to the analysis of elements from lithium of atomic number 3 through uranium of atomic number 92, the same cannot be applied to the analysis of hydrogen of atomic number 1.

Generally known surface analyzing methods applied to the analysis of specimens containing hydrogen include a secondary ion mass spectrometric method, an infrared absorption method, a high-speed ion impact recoil method, a nuclear reaction spectrometric method and an electron impact hydrogen desorption method. The secondary ion mass spectrometric method bombards the surface of a specimen by primary ions, such as cesium ions, and detects hydrogen ions sputtered as secondary ions from the surface of the specimen by a mass spectrometric method. The infrared absorption method detects hydrogen ions by using an infrared absorption spectrum. The high-speed ion impact recoil method bombards the surface of a specimen by high-speed ions accelerated by an accelerator and detects recoil hydrogen ions sputtered from the surface of the specimen. The nuclear reaction spectrometric method bombards the surface of a specimen by high-speed nitrogen ions and detects a rays emitted from the surface of the specimen by nuclear reaction. The electron impact hydrogen desorption method excites a molecular orbital of hydrogens and host atoms by bombardment with electrons with an energy on the order of 200 eV to cut the bonds between hydrogens and host atoms and detects hydrogen ions of 2 to 3 eV desorbed from the specimen.

The secondary ion mass spectrometric method is unable to achieve analysis through in situ observation. A hydrogen concentration measured by the infrared absorption method includes an error as large as 50% and the infrared absorption method is incapable of accurate analysis.

The high-speed ion impact recoil method and the nuclear reaction spectrometric method do not have drawbacks as those of the secondary ion mass spectrometric method and the infrared absorption method and are capable of accurately determining hydrogen distribution inside the specimen over the depth of about 1 $\mu$m with a depth resolution in the range of 50 to 500 Å. However, these two methods, unlike the Auger electron spectrometric method, need a large apparatus like an accelerator and cannot be easily equipped and handeld.

The electron impact hydrogen desorption method does not have any drawbacks like those in the secondary ion mass spectrometric method and the infrared absorption method and is capable of accurate, simple analysis through in situ observation. However, the electron impact hydrogen desorption method is able to analyze only a very thin hydrogen-containing layer of a thickness in the range of 2 to 3 Å and is incapable of analyzing inside of the specimen containing hydrogen.

SUMMARY OF THE INVENTION

The present invention has been made in view of those problems and it is therefore an object of the present invention to provide an electron impact elastic recoil hydrogen atom analyzer capable of achieving accurate depth distribution analysis of a specimen containing hydrogen through in situ observation.

According to one aspect of the present invention, an electron impact elastic recoil hydrogen atom analyzer comprises an electron beam projecting unit that projects an electron beam on the surface of a specimen containing hydrogen, for electron bombardment to make recoil hydrogen atoms emit from the specimen, and a hydrogen detecting unit that detects hydrogen atoms emitted from the specimen. Preferably, the electron impact elastic recoil hydrogen atom analyzer further comprises a data processing unit that determines the depth-distribution of hydrogen atoms contained in the specimen.

According to the present invention, the surface of the specimen is irradiated with the electron beam and energy distribution in the recoil hydrogen atoms emitted from the specimen is measured. Thus, hydrogen atoms contained in the specimen can accurately and easily be analyzed through practically useful in situ observation. Since the depth-distribution of hydrogen atoms in the specimen is determined on the basis of the result of detection, the hydrogen atoms contained inside the specimen, as well as those contained in a surface layer of the specimen, can accurately be analyzed with an appropriate depth resolution.

BRIEF DESCRIPTION OF THE DRAWINGS

The above and other objects, features and advantages of the present invention will become more apparent from the following description taken in connection with the accompanying drawings, in which:

FIG. 2 is a graph showing reference patterns of hydrogen energy distribution to be used by a data processing unit included in the electron impact elastic elastic recoil hydrogen atom analyzer shown in FIG. 1; and FIGS. 3A and 3B are graphs of assistance in explaining a method of determining the depth-distribution of hydrogen atoms contained in a specimen by using the reference patterns shown in FIG. 2.

DESCRIPTION OF THE PREFERRED EMBODIMENTS

Figure 1:
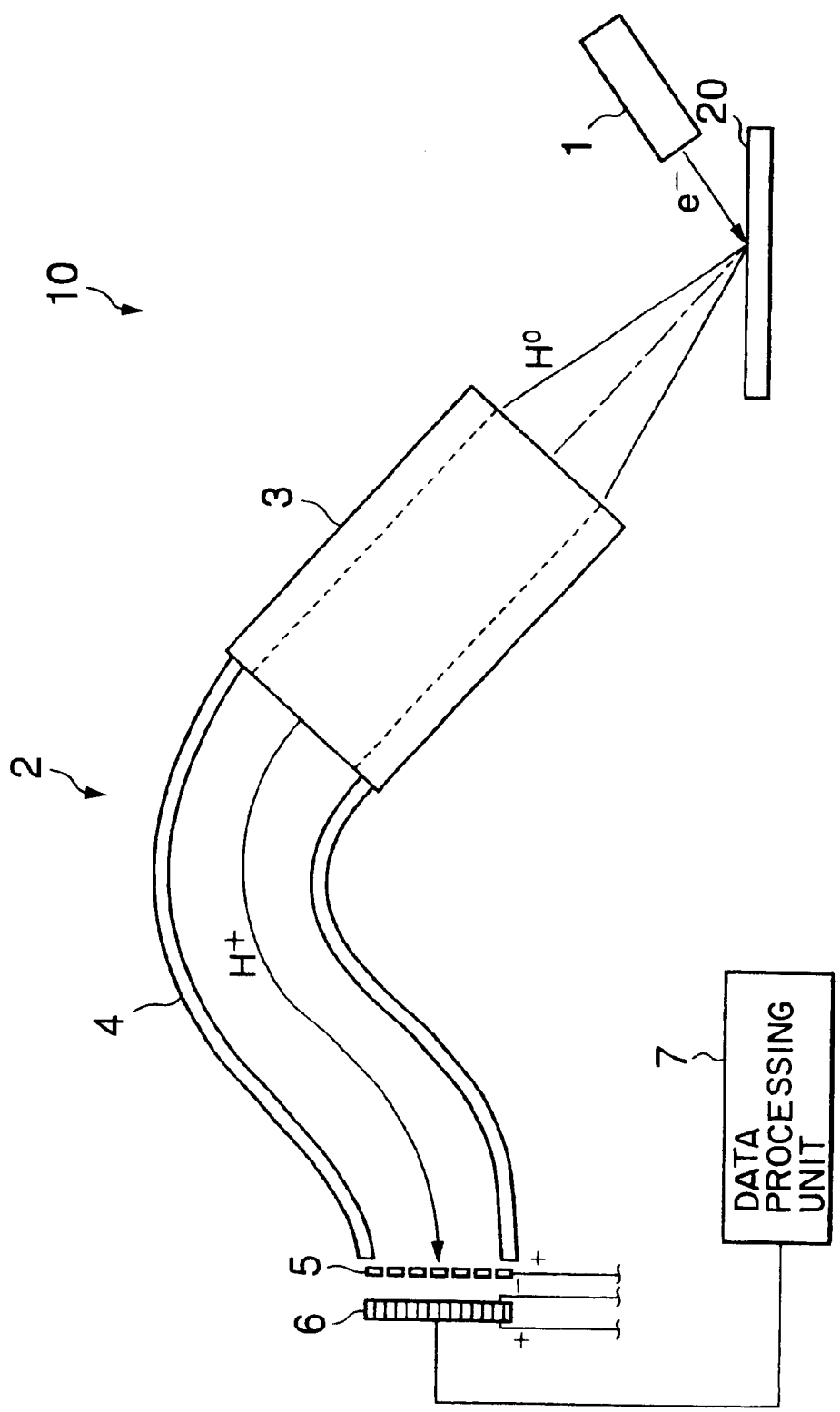
FIG. 1 is a schematic view of an electron impact elastic recoil hydrogen atom analyzer in a preferred embodiment according to the present invention.

Referring to FIG. 1, an electron impact elastic recoil hydrogen atom analyzer 10 in a preferred embodiment according to the present invention analyzes a specimen 20 of a hydrogenated semiconductor (a:Si-H). The electron impact elastic recoil hydrogen atom analyzer 10 comprises an electron gun (electron beam projecting device) 1 that projects an electron beam on the surface of the specimen 20, a hydrogen detector 2 for detecting hydrogen atoms $H^0$, and a data processing unit 7 for determining the depth-distribution of hydrogen in the specimen 20 on the basis of data provided by the hydrogen detector 2. Hydrogen atoms contained in the specimen 20 are made to elastically recoil by electron bombardment by the electron beam projected by the electron gun 1 on the surface of the specimen 20.

The hydrogen detector 2 comprises an ionizer 3 for ionizing hydrogen atoms emitted from the specimen 20, a deflector 4 for energy analysis of hydrogen ions $H^+$ produced by the ionizer 3, and an electron multiplying channel plate (ion detector) 6. The ionizer 3 may be operated by a known mechanism, such as a cylindrical B-A gage mechanism. The deflector 4 may be an electric field type deflector. Hydrogen ions are emitted from the ionizer 3 in a direction deviated from a direction toward the channel plate 6 to avoid the direct fall of heat flows issued from the ionizer 3 on the channel plate 6. A repelling mesh electrode 5 is disposed before the channel plate 6 and a positive bias of a predetermined magnitude is applied to the mesh electrode so as to reject ions with low energy to reach the surface of the channel plate 6. A high negative bias is applied to the detecting surface of the channel plate 6 to eliminate noise generated by electrons. Ions of residual gases may be ionized by the ionizer in addition to hydrogen atoms. However, the energy of the ions of residual gases is 1 eV or below and hence are rejected by the mesh electrode 5 to be detected by the channel plate 6.

The data processing unit 7 is a computer system, such as a personal computer capable of executing predetermined programs for a factor analysis. The data processing unit 7 determines a depth-distribution of hydrogen in the specimen 20 on the basis of a hydrogen energy distribution determined by the hydrogen detector 2 and reference patterns of hydrogen energy distribution prepared beforehand for depths in the specimen 20.

A method of determining the depth-distribution of hydrogen in the specimen 20 to be carried out by the data processing unit 7 will be described with reference to FIGS. 2, 3A and 3B. FIG. 2 shows reference patterns of hydrogen energy distribution to be used by the data processing unit 7 and FIGS. 3A and 3B are graphs of assistance in explaining the method of determining the depth-distribution of hydrogen contained in the specimen 20 by using the reference patterns shown in FIG. 2.

Referring to FIG. 2, energy distribution of hydrogen atoms emitted from the specimen 20 has predetermined different patterns $f_1$, $f_2$ and $f_3$, for example, for different depths in the ranges of 0 to 50 Å, 50 to 100 Å and 100 to 150 Å, respectively. The data processing unit 7 compares a hydrogen energy distribution f measured by the hydrogen detector 2 with the reference patterns $f_1$, $f_2$ and $f_3$ (see FIG. 3A) and determines weighting coefficients $\alpha_1$, $\alpha_2$ and $\alpha_3$ by using the following Expression (1).

$$f = \alpha_1 \times f_1 + \alpha_2 \times f_2 + \alpha_3 \times f_3 \tag{1}$$

The weighting coefficients $\alpha_1$, $\alpha_2$ and $\alpha_3$ thus determined correspond to relative hydrogen concentrations in the depths, respectively, in the specimen 20. Depth-distributions of hydrogen in the specimen 20 can be determined by multiplying the weighting coefficients $\alpha_1$, $\alpha_2$ and $\alpha_3$ by a predetermined constant t as shown in FIG. 3B.

In operation, the electron gun 1 projects an electron beam $e^-$ on the surface of the specimen 20 to make hydrogen atoms $H^0$ the specimen 20 elastically recoil by electron bombardment. Part of the hydrogen atoms emitted from the specimen 20 are detected by the hydrogen detector 2. The hydrogen detector 2 ionizes the hydrogen atoms by the ionizer 3 and deflects hydrogen ions $H^+$ produced by the ionizer 3 by the deflector 4. Then, the hydrogen ions deflected by the deflector 4 travel through the repelling mesh electrode 5 and fall on the channel plate 6. The channel plate 6 counts hydrogens. Data on hydrogen energy distribution provided by the deflector 4 and the channel plate 6 is given to the data processing unit 7. The data processing unit 7 determines depth-distribution of hydrogen in the specimen 20 on the basis of the predetermined reference patterns of hydrogen energy distributions for different depths.

The recoil energy $E_R$ of hydrogen is expressed by the following Expression (2).

$$E_R = 4 \frac{M_1 M_2}{(M_1 + M_2)^2} E_1 \cos^2 \phi \tag{2}$$

where $E_1$ is the energy of the electron beam projected by the electron gun 1, $M_1$ is the mass of electrons, $M_2$ is the mass of hydrogen atoms and $\phi$ is recoil angle.

Since $M_2$ is far greater than $M_1$, Expression (2) can be rewritten as follows.

$$E_R \approx 4 \frac{M_1}{M_2} E_1 \cos^2 \phi \tag{3}$$

In Expression (3), $M_1 = M_2/1836$. Therefore, A maximum value of $E_R$ when $\cos^2 \phi = 1$ is expressed by the following Expression (4)

$$E_R \approx \frac{E_1}{459} \tag{4}$$

As obvious from Expression (4), recoil energy $E_R$ of hydrogen is proportional to the energy $E_1$ of the electron beam. Therefore, when the energy $E_1$ of the electron beam is increased, hydrogen atoms in deeper positions can be emitted accordingly. More concretely, a maximum value of the recoil energy $E_R$ is about 22 eV when the energy $E_1$ of the electron beam is 10 keV and hydrogen distribution in a depth of several tens angstroms of the specimen 20 can be analyzed. A maximum value of the recoil energy $E_R$ is about 65 eV when the energy $E_1$ of the electron beam is 32 keV and hydrogen distribution in a depth in the range of 200 to 300 Å of the specimen 20 can be analyzed.

The electron impact elastic recoil hydrogen atom analyzer 10 in this embodiment projects the electron beam on the surface of the specimen 20 and determines the energy distribution of recoil hydrogen atoms emitted by electron bombardment. Therefore, the hydrogen contained in the specimen 20 can accurately and easily be analyzed by practically useful in situ observation.

The electron impact elastic recoil hydrogen atom analyzer 10 in this embodiment determines the depth-distribution of hydrogen contained in the specimen 20 on the basis of the hydrogen energy distribution thus determined and the predetermined reference patterns of hydrogen energy distributions. Therefore, the hydrogen distribution inside the specimen 20 as well as that on the surface of the specimen 20 can accurately be analyzed with an appropriate depth resolution.

In the electron impact elastic recoil hydrogen atom analyzer 10 in this embodiment, the energy of the electron beam projected by the electron gun 1 may selectively determined according to the depth of a part of the specimen 20 to be measured and depth resolution. For example, hydrogen distribution in a depth of several tens angstroms in the specimen 20 can be measured in a depth resolution of about 10 Å when the energy $E_1$ of the electron beam is 10 keV. Hydrogen distribution in a depth in the range of 200 to 300 Å in the specimen 20 can be measured in a depth resolution of about 50 Å when the energy $E_1$ of the electron beam is 32 keV.

Although the invention has been described in its preferred embodiment with a certain degree of particularity, obviously any changes and variations are possible therein. It is therefore to be understood that the present invention may be practiced otherwise than as specifically described herein without departing from the scope and spirit thereof.

What is claimed is:

1. An electron elastic impact recoil hydrogen atom analyzer comprising:
   an electron beam projecting unit for projecting an electron beam on a surface of a specimen containing hydrogen, for electron bombardment to make hydrogen atoms contained in the specimen recoil; and
   a hydrogen detecting unit for detecting hydrogen atoms emitted from the specimen.

2. The electron impact elastic recoil hydrogen atom analyzer according to claim 1, wherein the hydrogen detecting unit includes an ionizer for ionizing hydrogen atoms emitted from the specimen, and an ion detector for detecting hydrogen ions produced by the ionizer.

3. The electron impact elastic recoil hydrogen atom analyzer according to claim 2, wherein the ionizer is a cylindrical B-A gage mechanism.

4. The electron impact elastic recoil hydrogen atom analyzer according to claim 2, wherein the ion detector is an electron multiplying channel plate.

5. The electron impact elastic recoil hydrogen atom analyzer according to claim 4, wherein a high negative bias is applied to a front surface of the electron multiplying channel plate.

6. The electron impact elastic recoil hydrogen atom analyzer according to claim 5, wherein a repelling mesh electrode biased by a positive bias is disposed before the electron multiplying channel plate.

7. The electron impact elastic recoil hydrogen atom analyzer according to claim 2, wherein the hydrogen detecting unit further includes a deflector for energy analysis of hydrogen ions produced by ionizing hydrogen atoms by the ionizer, and the ion detector detects the hydrogen ions deflected by the deflector.

8. The electron impact elastic recoil hydrogen atom analyzer according to claim 5, wherein the deflector is an electric field type deflector.

9. The electron impact elastic recoil hydrogen atom analyzer according to claim 1, further comprising a data processing unit for determining a depth-distribution of hydrogen contained in the specimen on the basis of data provided by the hydrogen detecting unit.

10. The electron impact elastic recoil hydrogen atom analyzer according to claim 9, wherein the data processing unit determines the depth-distribution of hydrogen contained in the specimen on the basis of a hydrogen energy distribution determined by the hydrogen detecting unit and predetermined reference patterns of hydrogen energy distribution at different depths in the specimen.

11. The electron impact elastic recoil hydrogen atom analyzer according to claim 1, wherein the specimen is a piece of a hydrogenated semiconductor.

* * * * *